(12) United States Patent
Carll

(10) Patent No.: US 6,670,171 B2
(45) Date of Patent: Dec. 30, 2003

(54) DISPOSABLE VESSEL

(75) Inventor: Kenneth B. Carll, Bridgeton, NJ (US)

(73) Assignee: Wheaton USA, Inc., Millville, NJ (US)

( * ) Notice: Subject to any disclaimer, the term of this patent is extended or adjusted under 35 U.S.C. 154(b) by 0 days.

(21) Appl. No.: 09/901,767

(22) Filed: Jul. 9, 2001

(65) Prior Publication Data

US 2003/0008389 A1 Jan. 9, 2003

(51) Int. Cl.[7] .................................................. C12M 1/02
(52) U.S. Cl. ................. 435/289.1; 435/383; 435/302.1; 366/243; 366/273; 366/343; 366/348
(58) Field of Search ..................... 435/302.1, 383, 435/394, 289.1, 304.1, 292.1; 366/273, 274, 275, 276, 308, 326.1, 343, 243, 256, 242, 348

(56) References Cited

U.S. PATENT DOCUMENTS

| | | | | |
|---|---|---|---|---|
| 1,705,162 A | * | 3/1929 | Wahl | 366/118 |
| 3,384,354 A | * | 5/1968 | Migule et al. | 366/118 |
| 3,514,080 A | * | 5/1970 | Price et al. | 366/169.1 |
| 3,572,651 A | | 3/1971 | Harker | |
| 3,854,704 A | * | 12/1974 | Balas | 366/102 |
| 4,184,916 A | | 1/1980 | Tolbert et al. | |
| 4,289,854 A | * | 9/1981 | Tolbert et al. | 435/289.1 |
| 4,355,906 A | | 10/1982 | Ono | |
| 4,417,861 A | | 11/1983 | Tolbert | |
| 4,483,623 A | | 11/1984 | Eaton et al. | |
| 4,596,779 A | | 6/1986 | Ono | |
| 4,597,399 A | * | 7/1986 | Rabenau et al. | 134/184 |
| 4,649,118 A | * | 3/1987 | Anderson | 366/255 |
| 4,759,635 A | | 7/1988 | MacMichael et al. | |
| 4,783,172 A | | 11/1988 | Garg | |
| 4,910,147 A | | 3/1990 | Bacehowski et al. | |
| 4,939,151 A | | 7/1990 | Bacehowski et al. | |
| 4,968,624 A | | 11/1990 | Bacehowski et al. | |
| 5,008,197 A | | 4/1991 | Wergeland et al. | |
| 5,153,131 A | | 10/1992 | Wolf et al. | |
| 5,167,449 A | | 12/1992 | Killough | |
| 5,225,346 A | | 7/1993 | Matsumiya et al. | |
| 5,267,791 A | | 12/1993 | Christian et al. | |
| 5,288,296 A | * | 2/1994 | McCabe et al. | 435/252.2 |
| 5,375,926 A | * | 12/1994 | Omasa | 366/118 |
| 5,518,893 A | | 5/1996 | Park et al. | |
| 5,523,228 A | | 6/1996 | Ingram et al. | |
| 5,576,211 A | | 11/1996 | Falkenberg et al. | |
| 6,146,875 A | * | 11/2000 | Ward | 383/104 |

FOREIGN PATENT DOCUMENTS

| | | | |
|---|---|---|---|
| EP | 0 053 869 A2 | * | 6/1982 |
| GB | 2 202 549 A | * | 9/1988 |

* cited by examiner

Primary Examiner—William H. Beisner
(74) Attorney, Agent, or Firm—RatnerPrestia

(57) ABSTRACT

The present invention relates to an improved vessel for cell culture and methods for its use. The vessel of the present invention comprises a collapsible bag with an inner surface, an outer surface and a top periphery and a headplate having a circumferential edge wherein the top periphery of the bag is sealed to the edge of the headplate. The present invention also relates to an impeller for use with the vessel and a method for culturing cells.

27 Claims, 8 Drawing Sheets

DISPOSABLE VESSEL

FIELD OF INVENTION

The present invention relates to laboratory vessels. More specifically, the present invention relates to an improved vessel for cell culture and methods for its use.

BACKGROUND OF THE INVENTION

There are two major types of cells grown in vitro: suspension cells (anchorage-independent cells); and adherent cells (anchorage-dependent cells). Suspension or anchorage-independent cells can proliferate, in vitro, without being attached to a surface. In contrast, adherent or anchorage-dependent cells require attachment to a surface in order to grow in vitro.

Suspension or anchorage-independent cells have typically been grown in vitro in glass, metal, or hard plastic vessels. There have been disadvantages, however, to using these cell culture vessels. Glass and metal cell culture vessels are expensive and require maintenance, as they are not disposable or sterile. In order to maintain a sterile or aseptic environment for cell culture, the vessels require sterilization, usually by autoclave. Therefore, the cell culture vessels must be washed and sterilized prior to and/or subsequent to their use. In addition, because glass and metal cell culture vessels are not disposable, it is necessary to have adequate space for storage of the glass and metal vessels. Thus, as glass, metal, and hard plastic cell culture vessels are expensive, not disposable, and require extensive maintenance, there has been a need for a cell culture vessel that is inexpensive, disposable, collapsible, and pre-sterilized.

Further, for anchorage-independent biological cells to grow, the cells require constant suspension. In order for the cells to remain suspended, a cell culture vessel must have means for keeping the cells suspended. Many cell culture vessels have an impeller with blades that rotate to keep cells suspended. If the impeller rotation or movement is too strong or the blades are too rigid or too long, the cells may be sheared by the force of the impeller or blades. Likewise, if the impeller rotation or movement is too weak or the blades are too short, the cells may not remain suspended. Therefore, there is a need for an improved cell culture vessel which provides gentle stirring to prevent shearing and keep cells suspended.

SUMMARY OF THE INVENTION

The present invention provides a vessel for cell culture comprising a collapsible bag with an inner surface, an outer surface, a top periphery and a headplate having a circumferential edge wherein the top periphery of the bag is sealed to the edge of the headplate. The present invention also provides an impeller comprising a hollow flexible shaft having a top region and a bottom region, wherein the bottom region comprises a flexible blade. The present invention further provides a method of mixing a fluid comprising the steps of providing a vessel having a collapsible bag containing an impeller comprised of a hollow flexible shaft, inserting a magnet into the hollow shaft of the impeller, introducing an external, adjustable magnetic source to interact with the magnet and cause the magnet and the hollow shaft to move.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawing in which:

DETAILED DESCRIPTION OF THE INVENTION

The present invention provides a vessel for cell culture comprising a collapsible bag with an inner surface, an outer surface, a top periphery and a headplate. The bag has a circumferential edge wherein the top periphery of the bag is sealed to the edge of the headplate. The present invention also provides an impeller comprising a hollow flexible shaft having a top region and a bottom region, wherein the bottom region comprises a flexible blade. The present invention further provides a method of mixing a fluid comprising the steps of providing a vessel having a collapsible bag containing an impeller comprised of a hollow flexible shaft, inserting a magnet into the hollow shaft of the impeller, introducing an external, adjustable magnetic source to interact with the magnet and cause the magnet and the hollow shaft to move. The method may also include the removal of the magnet from the hollow shaft of the impeller prior to disposal of the vessel.

The vessel according to an exemplary embodiment of the present invention has an impeller with thin, flexible blades and a hollow shaft in which a reusable magnet can be placed. The presence of a magnet within the shaft of the impeller and the presence of a restricting means disposed on the shaft of the impeller, such as an o-ring, allows the gentle rotation of the impeller and the subsequent undulation of the flexible blades when an adjustable magnetic force, such as a magnetic stir plate, is applied to the vessel. This creates a gentle stirring of the cells, which keeps the cells in suspension and prevents the cells from shearing.

Figure 1:
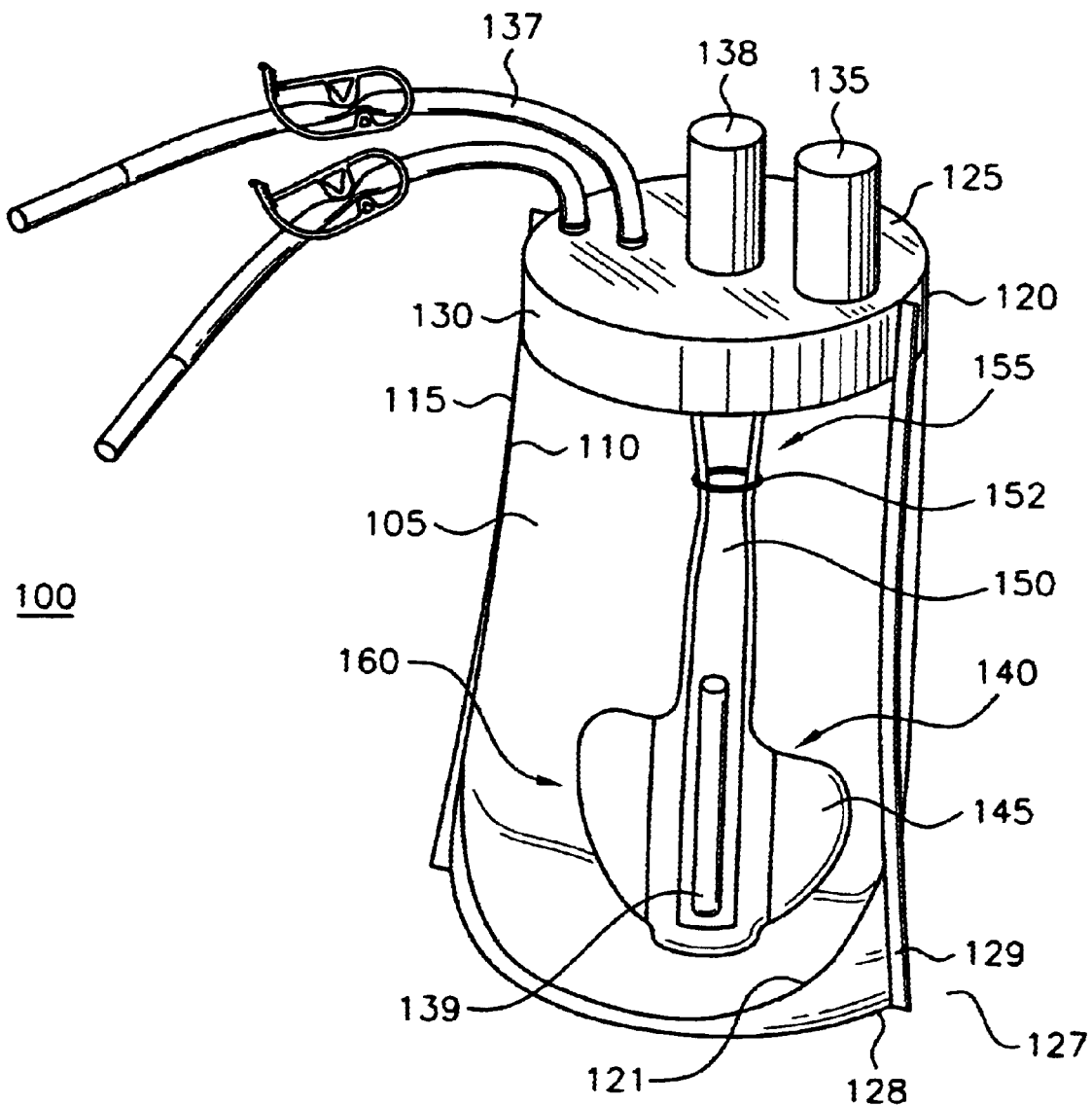
FIG. 1 illustrates one embodiment of the present invention.

FIG. 1 shows a vessel 100 for cell culture comprising a collapsible bag 105 with an inner surface 110, an outer surface 115, a top periphery 120 and a headplate 125. Headplate 125 has a circumferential edge 130 to which top periphery 120 of bag 105 is sealed. One method of sealing includes simply melting edge 130 to headplate 125. Other methods could be used, however, including glue, hot-melt adhesives, or other sealing methods as understood by those skilled in the art. Collapsible bag 105 further comprises a bottom 127 with outer edges 128 which allow bag 105 to be free standing. Typical to the exemplary embodiment, outer edges 128 are formed when bag 105 is constructed. Bag 105 is formed from a collapsible plastic and sealed along its seams 129. The lower part of those seams forms the stabilization, or platform, for bag 105. Other methods of insuring the upright stabilization of bag 105 could be envisioned, which are consistent with this invention, include the use of a base similar to headplate 125.

It is important, however, that low flow regions or eddy pockets are avoided to insure good mixing within the vessel. FIG. 1, for example, shows that the bag 105 does not extend into outer edges 128. Moreover, bottom 121 of inner surface 110 is rounded to achieve good mixing.

In one embodiment of the present invention, vessel 100 is comprised of polyethylene. In addition, vessel 100 can be pre-sterilized. As most cell culture procedures are carried out under aseptic conditions by practicing the so-called sterile technique, the pre-sterilization of vessel 100 provides the culture chamber and the fluid pathway to be maintained in a sterile, closed environment. Because the most optimal objective is to have the culture process carried out in a system where the culture chamber and fluid path is functionally closed to the external environment, with the sterile integrity maintained from the time the device is manufactured until it has been disposed of, the collapsibility and disposability of vessel 100 is ideal for pre-sterilization. One method of pre-sterilizing includes gamma irradiation. Other methods known to those skilled in the art could also be used.

In another embodiment, headplate 125 comprises at least one port 135. Port 135 can be used in accordance with the present invention for filling vessel 100. Port 137 can be a port for gas supply. In this exemplary embodiment, port 138 also allows the insertion of magnet 139. These are just an example of the many different ports which can be provided in headplate 125. One skilled in the art would know the requirements for a particular cell culture and could easily provide the necessary ports for a particular application.

In the exemplary embodiment, vessel 100 contains impeller 140 having a flexible blade 145. Flexible blade 145 can be comprised of polyethylene. Flexible blade 145 can be a single blade, a pair of blades, or multiple blades. Impeller 140 is comprised of a hollow flexible shaft 150 having a top region 155 and a bottom region 160, with top region 155 connected to headplate 125 and flexible blade 145 connected to bottom region 160 of shaft 150. In an exemplary embodiment of the present invention, flexible blade 145 is contiguous with shaft 150. Shaft 150 of impeller 140 can contain magnet 139. In the exemplary embodiment of the present invention, top region 155 of shaft 150 comprises means for restricting movement of shaft 150 to a generally periodic pendulum-like, but elliptical rotation. According to the present invention, means for restricting movement of shaft 150 can be an o-ring 152, a notch, or other means which create a relative weak point in top region 155 of shaft 150 of impeller 140 to prevent twisting of impeller 140.

Figure 2:
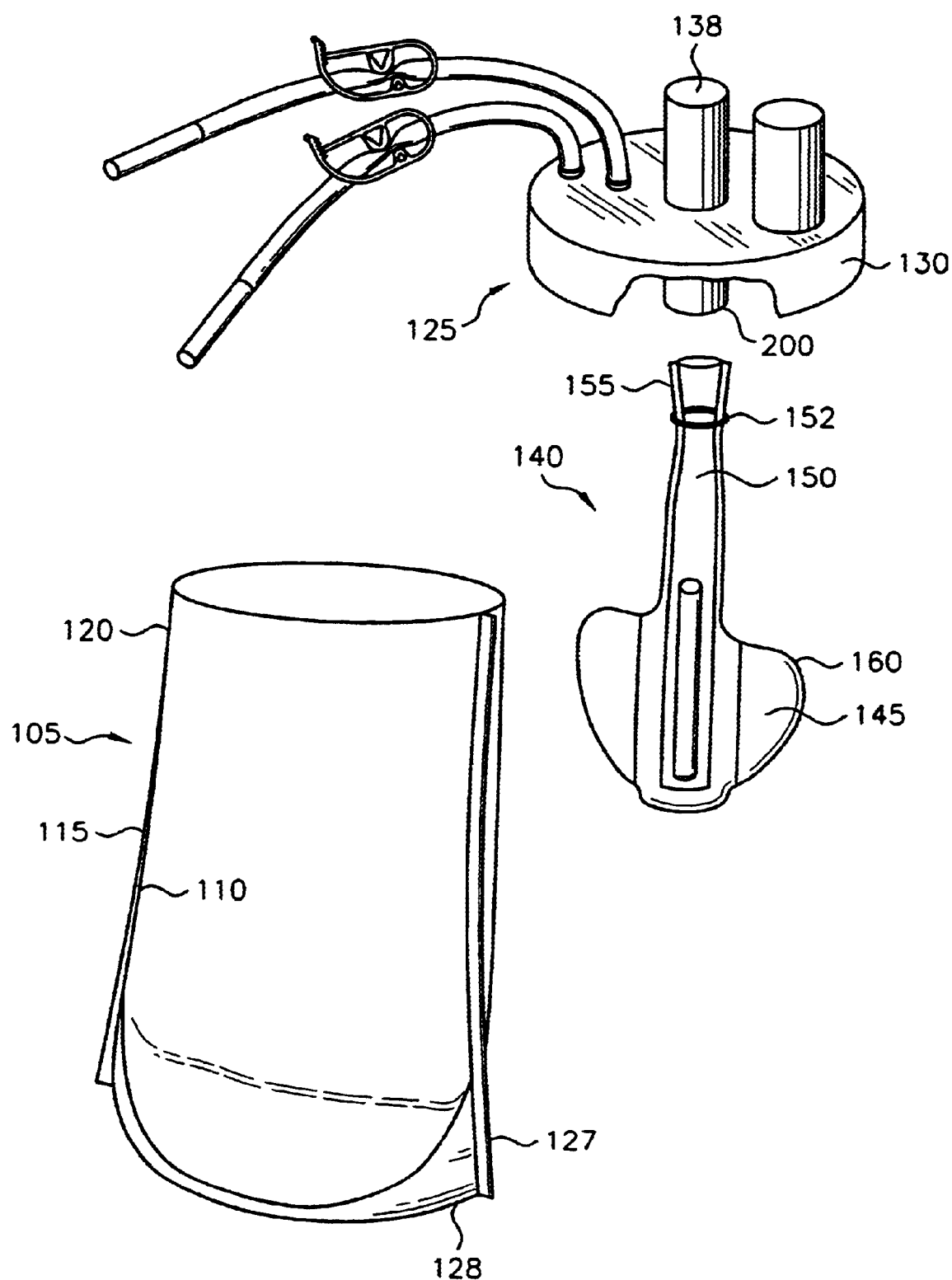
FIG. 2 illustrates the components of the vessel of the present invention.

FIG. 2 shows the components of vessel 100. The components of vessel 100, as discussed above, are collapsible bag 105, headplate 125, and impeller 140. Bag 105 comprises an inner surface 110, an outer surface 115, and a top periphery 120. As discussed above, top 120 of bag 105 can be heat sealed or otherwise attached to edge 130 of headplate 125. Bottom 127 of bag 105 can have outer edges 128 to support bag 105. Outer edges 128 form a triangular-like shape at the corners of outer surface 115 of bag 105, which are separate from inner surface 110 of bag 105. Impeller 140 is comprised of a hollow flexible shaft 150 having a top region 155 and a bottom region 160, wherein top region 155 is connected to the bottom 200 of port 138 of headplate 125, for example by heat sealing, and bottom region 160 of shaft 150 is connected to flexible blade 145.

Figure 3:
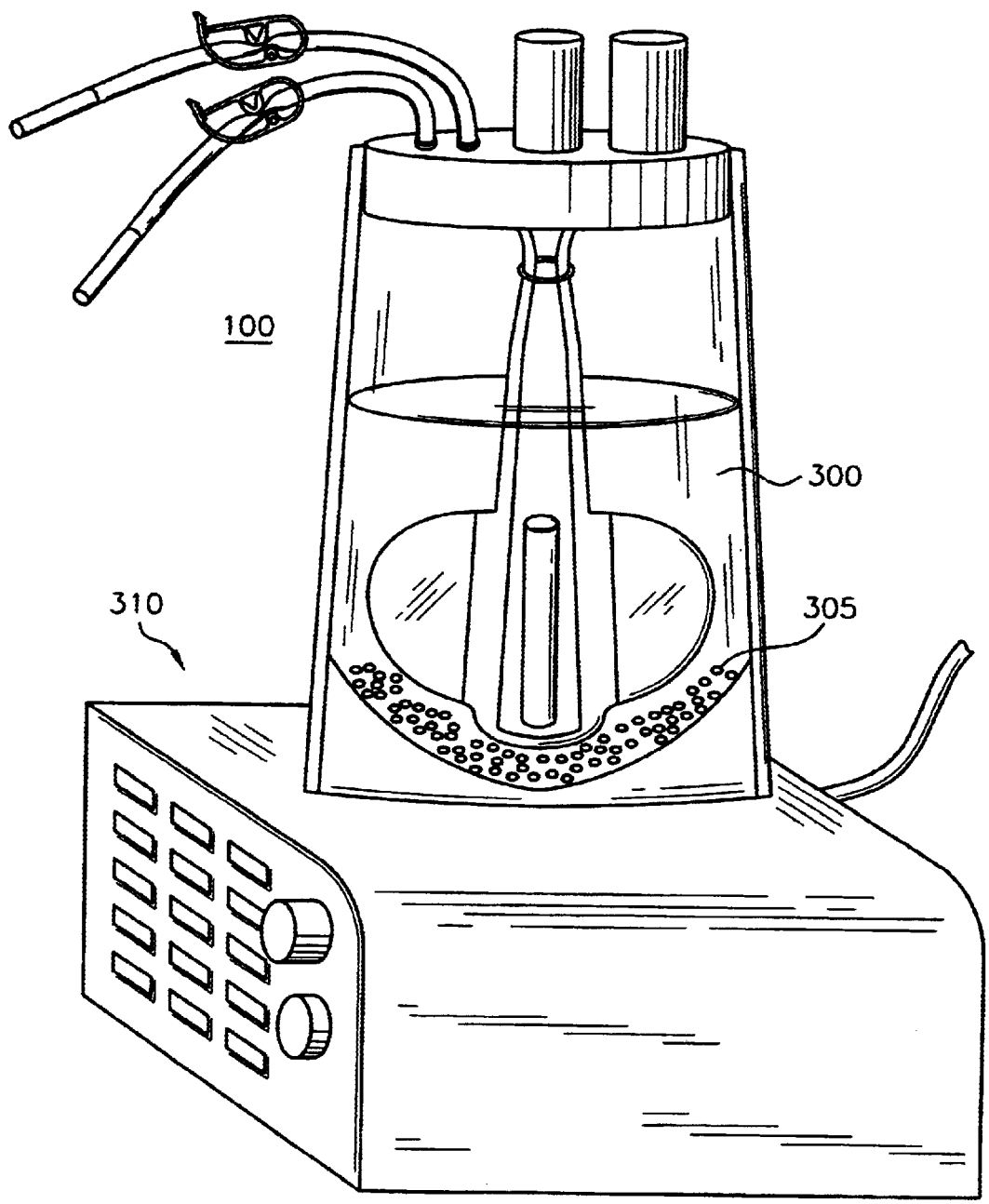
FIG. 3 shows the vessel of the present invention filled with a fluid and containing particles on an adjustable magnetic stir plate.

FIG. 3 shows vessel 100 filled with a fluid 300 and particles 305 on an adjustable magnetic stir plate 310. In this embodiment, fluid 300 is a cell culture medium and particles 305 are biological cells.

Figure 4A:
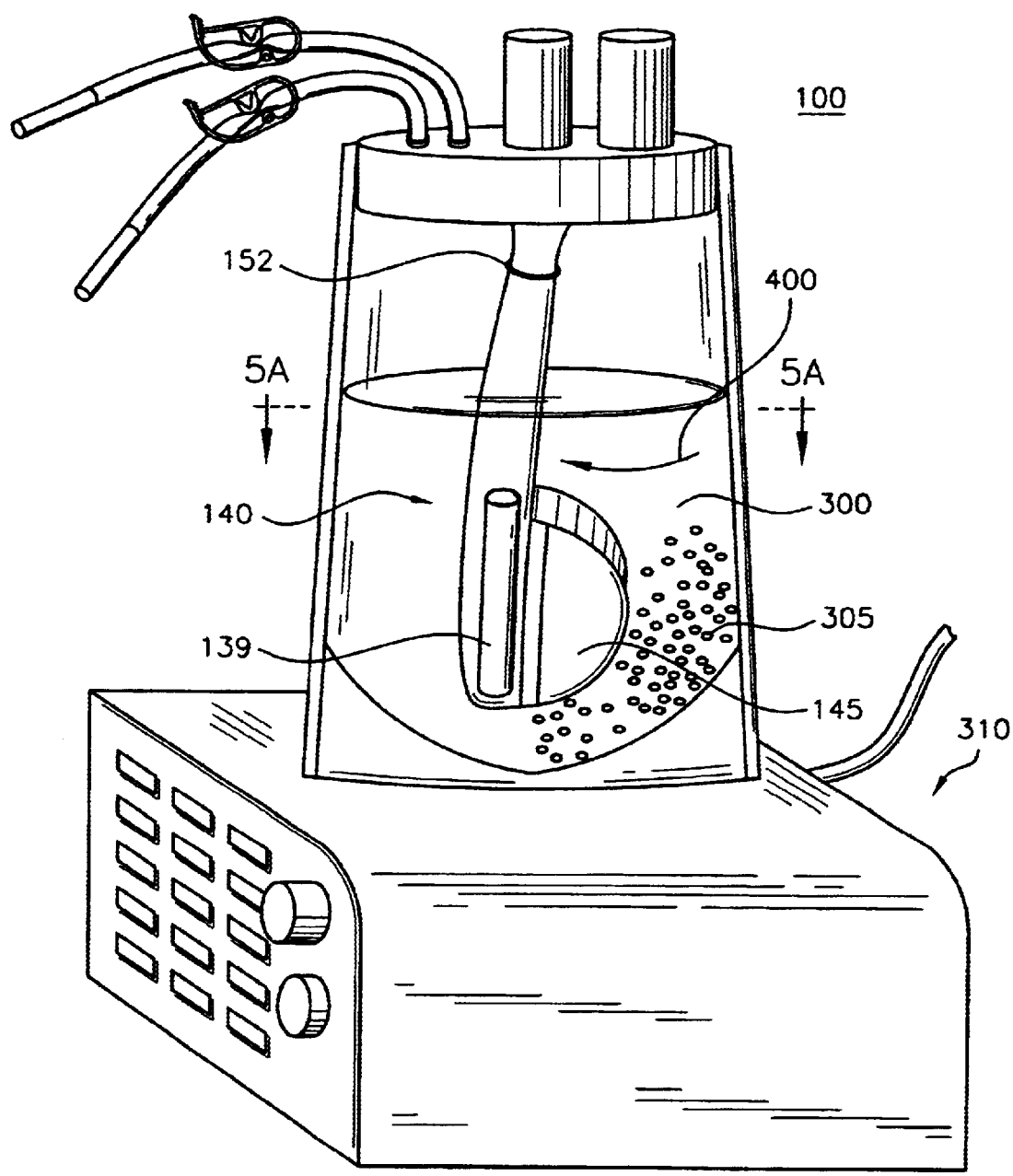
FIG. 4A is a partial side view of a vessel according to the present invention depicting a first movement of the rotation of the impeller, flexible blades and particles as a magnetic force is applied to the vessel.
Figure 4B:
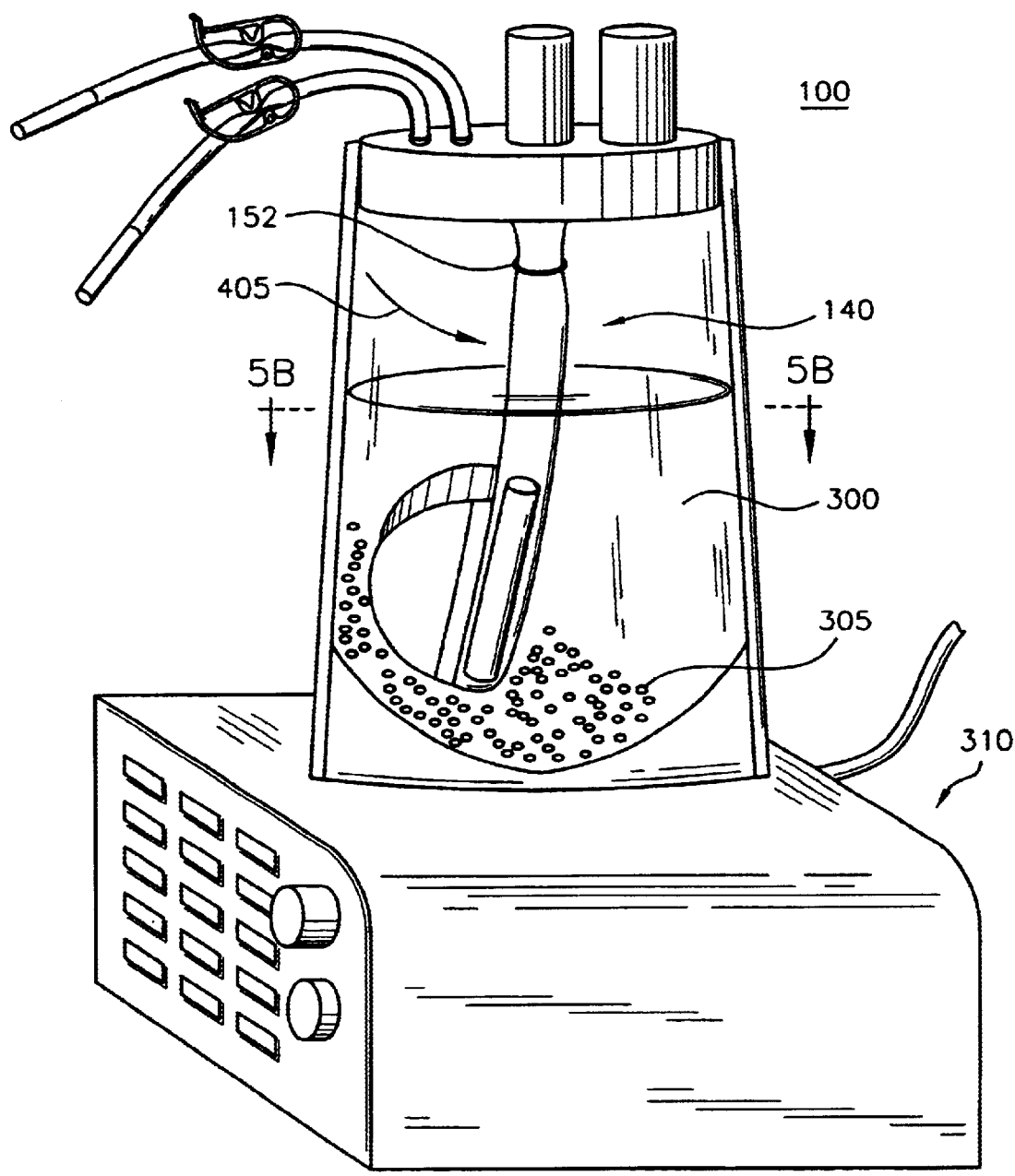
FIG. 4B is a partial side view of a vessel according to the present invention depicting the continued movement of the rotation of the impeller, flexible blades and particles as a magnetic force is applied to the vessel.
Figure 4C:
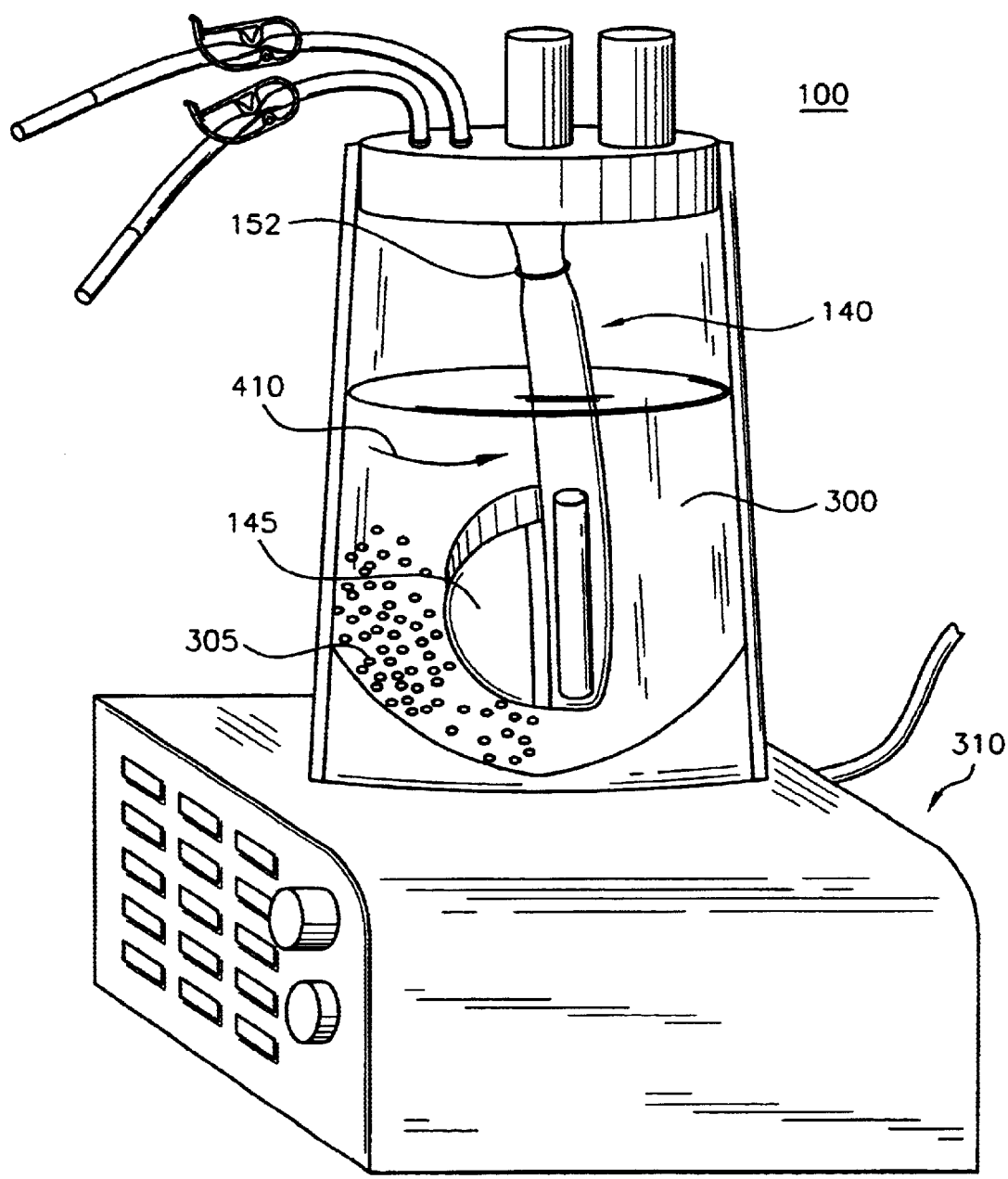
FIG. 4C is a partial side view of a vessel according to the present invention depicting the continued movement of the rotation of the impeller, flexible blades and particles as the magnetic force causes the impeller to move in the opposite direction of the rotation depicted in FIG. 4B.
Figure 4D:
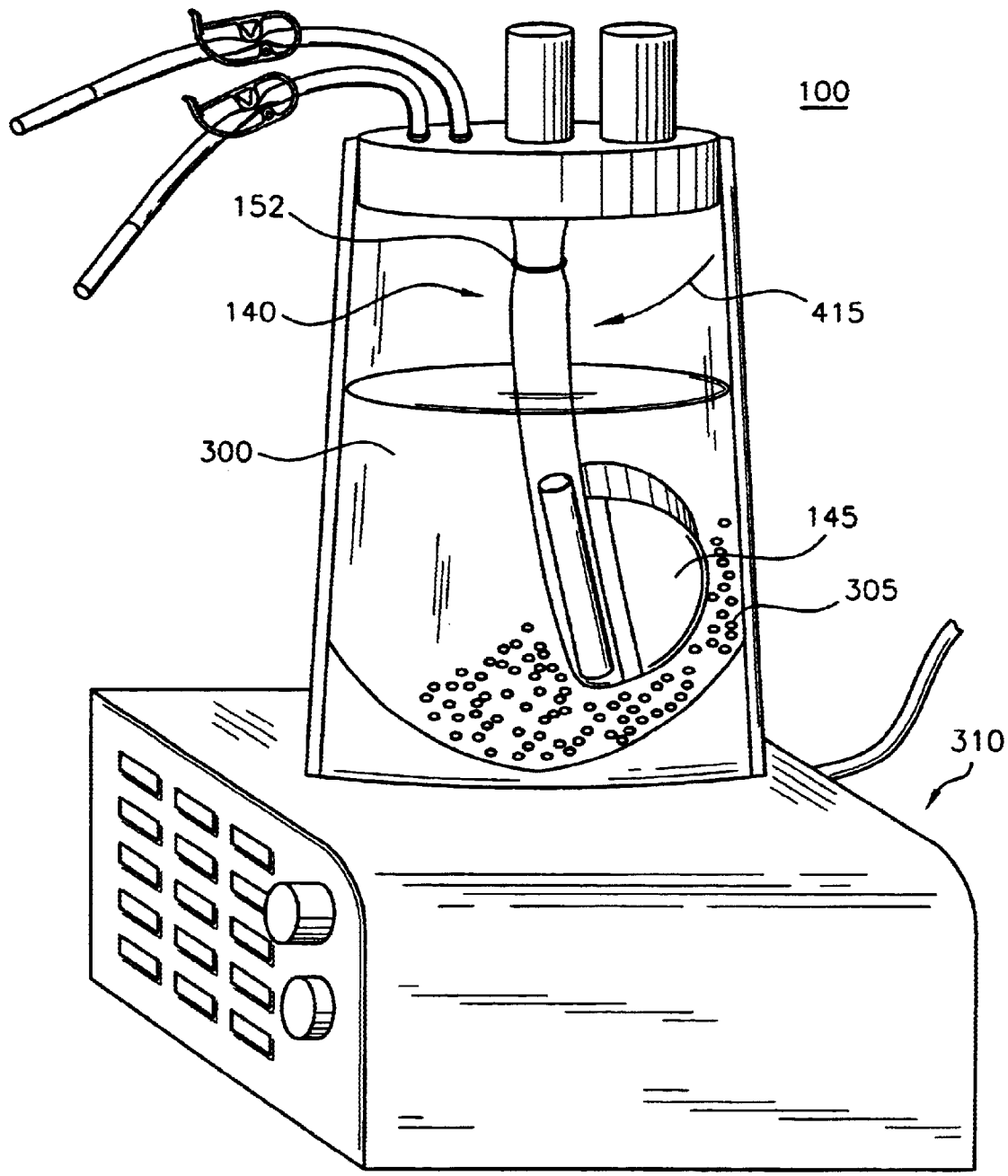
FIG. 4D is a partial side view of a vessel according to the present invention depicting the continued movement of the rotation of the impeller, flexible blades and particles as depicted in FIG. 4C as a magnetic force is applied to the vessel.

FIGS. 4A–4D show the sequential movements of flexible blade 145 of shaft 150 of impeller 140 in vessel 100 and of particles 305 when a magnetic force is applied to vessel 100 with an adjustable magnetic stir plate 310. Adjustable magnetic stir plate 310 includes a bar magnet mounted on a shaft, which is driven by a motor. Those skilled in the art are familiar with such stir plates. The speed of the motor is generally controlled by a rheostat. According to the present invention, and as demonstrated in FIG. 4A, when a magnetic force, such as adjustable magnetic stir plate 310, is applied to vessel 100, the rotation of the bar magnet (not shown) within magnetic stir plate 310 causes rotational, elliptical movement of magnet 139 within vessel 100. The movement of magnet 139 in response to rotation of the magnet in stir plate 310 causes impeller 140 to begin to move in an elliptical pendulum-like rotation. When impeller 140 moves in the direction of arrow 400, fluid resistance against flexible blades 145 forces flexible blades 145 to move in the opposite direction of arrow 400, causing the stirring of particles 305. FIG. 4B shows that when impeller 140 begins to move in the direction of arrow 405, flexible blades 145 and particles 305 are forced in the opposite direction of arrow 405. FIG. 4C shows impeller 140 continuing to move through the elliptical pendulum-like rotation. As impeller 140 continues to move in the direction of arrow 410, flexible blades 145 and particles 305 are forced in the opposite direction of arrow 410. FIG. 4D shows impeller 140 continuing through the elliptical pendulum-like rotation and beginning to move in the direction of arrow 415. Likewise, flexible blades 145 and particles 305 are forced in the opposite direction of arrow 415. The continuous movement of impeller 140 and flexible blades 145 throughout the elliptical pendulum-like rotation results in the continuous suspension of particles 305.

As shown in FIGS. 4A–4D, the presence of a constricting device 152 creates a sort of "pivot point" or "weak point" along the shaft. This device affects the movement of impeller 140 when magnet 139 and an adjustable external magnetic force, such as stir plate 310, interact. The result is an elliptical pendulum-like rotation of impeller 140. Constricting device 152 could take many forms, including a ring or knotted piece of material. An exemplary constricting device would be a typical o-ring, placed around the shaft. Alternatively, a notch in the shaft itself could create the "pivot point" which allows the elliptical, pendulum-like rotation desired. The result of the elliptical pendulum-like rotation of impeller 140 is the gentle motion of flexible blades 145 and the gentle stirring of fluid 300 and particles 305. The gentle motion of flexible blades 145 and the gentle stirring of fluid 300 and particles 305 is essential when fluid 300 is a cell culture medium and particles 305 are biological cells.

Figure 5B:
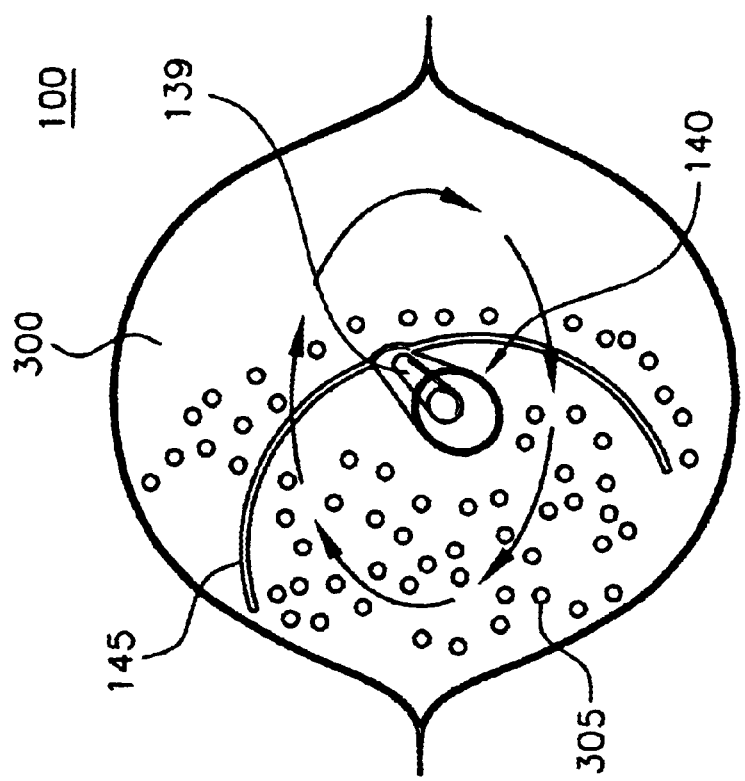
FIG. 5B is a top view of a vessel according to the present invention depicting the movement of the impeller, flexible blades and particles through an opposite rotation as a magnetic force is applied to the vessel as depicted in FIG. 5A.
Figure 5A:
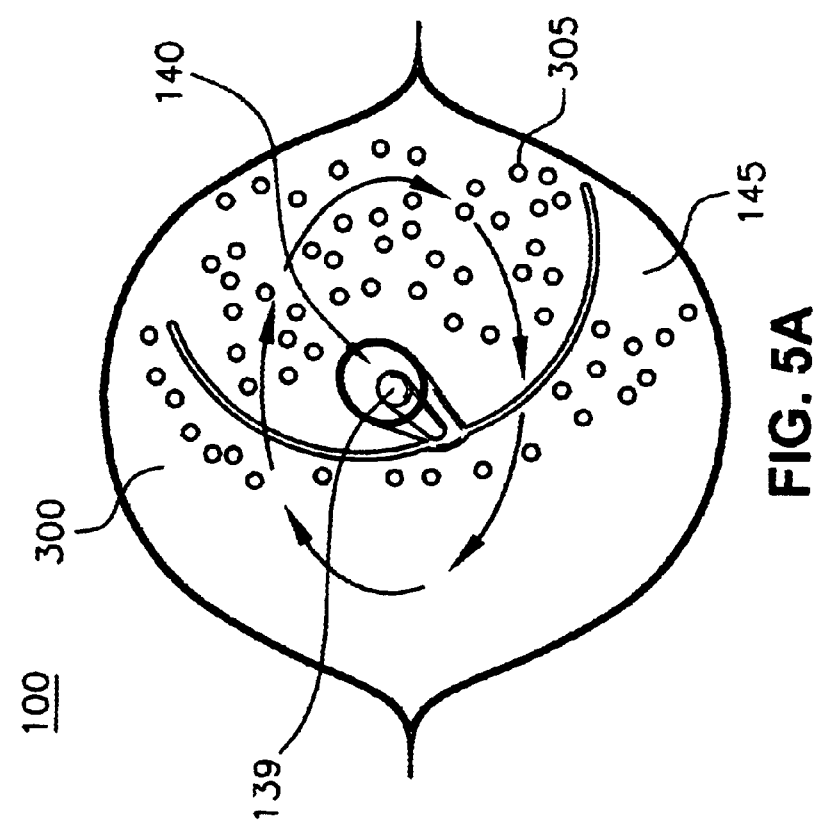
FIG. 5A is a top view of a vessel according to the present invention depicting the movement of the impeller, flexible blades and particles through a first rotation as a magnetic force is applied to the vessel.

FIGS. 5A and 5B show a top view of vessel 100 demonstrating the elliptical pendulum-like rotation of impeller 140 and the effect of the rotation of the magnet in the stir plate on flexible blades 145 and particles 305 when a magnetic force is applied to vessel 100.

The present invention also relates to an impeller 140 comprising a hollow flexible shaft 150 having a top region 155 and a bottom region 160, wherein bottom region 160 comprises a flexible blade 145. Impeller 140 may be comprised of polyethylene. In an exemplary embodiment, bottom region 160 of impeller 140 comprises two flexible blades 145. Hollow flexible shaft 150 of impeller 140 may also contain magnet 139 and magnet 139 may be removable. The ability to remove magnet 139 from impeller 140 allows for the disposal of impeller 140 and the ability to reuse magnet 139 with additional impellers or vessels. The ability to reuse magnet 139 is also advantageous, as the disposal of magnet 139 adds additional cost if it has to be replaced with each use.

The present invention also relates to a method of mixing a fluid. First a vessel is provided which comprises a collapsible bag containing an impeller comprised of a hollow flexible shaft. A magnet is then inserted into the hollow shaft of the impeller. An external adjustable magnetic source, such as a magnetic stir plate, is introduced to interact with the magnet and cause the hollow shaft to move. The magnet is then removed from the hollow shaft of the impeller. The method may further comprise a vessel with a headplate and a hollow flexible shaft of an impeller with a top region and a bottom region, wherein the top region is connected to the headplate.

The present invention also relates to the preferred method of use of the vessel of the present invention, which is a method of culturing cells. First a pre-sterilized vessel is provided which comprises a collapsible bag with a headplate and an impeller comprised of a hollow flexible shaft having a top region and a bottom region, wherein the top region is connected to the headplate and wherein the bottom region comprises a flexible blade. A magnet is then inserted into the hollow shaft of the impeller and a cell line and media is introduced into the vessel through a fill port. The cell line is then allowed to proliferate. The cell line and media are removed from the vessel. Finally, the magnet is removed from the hollow shaft of the impeller through the impeller magnet port and the vessel is disposed.

Although the present invention has been particularly described in conjunction with specific preferred embodiments, it is evident that many alternatives, modifications, and variations will be apparent to those skilled in the art. It is therefore contemplated that the appended claims will embrace any such alternatives, modifications, and variations as falling within the true scope and spirit of the present invention.

What is claimed is:

1. A vessel for cell culture comprising:
    a headplate having a circumferential edge;
    a collapsible bag with an inner surface, an outer surface and a top periphery, said top periphery of said bag sealed to said edge of said headplate; and
    an impeller comprised of a flexible blade and a hollow flexible shaft, said shaft having a top region, a bottom region, and a central axis, said impeller attached to said headplate at said shaft's top region such that said impeller does not rotate about its central axis.

2. The vessel of claim 1 wherein said flexible blade is connected to said bottom region of said shaft.

3. The vessel of claim 1 wherein said flexible blade is contiguous with said shaft.

4. The vessel of claim 1 wherein said shaft contains a magnet.

5. The vessel of claim 1 wherein said top region of said shaft comprises means for restricting movement of said shaft to a periodic pendulum-like rotation.

6. The vessel of claim 5 wherein said means comprises an o-ring.

7. A vessel for cell culture comprising:
    a headplate;
    a pre-sterilized collapsible bag sealed to said headplate;
    an impeller comprising a hollow flexible shaft connected to said headplate;
    two flexible blades attached to said impeller; and
    a constriction device o-ring disposed on said flexible shaft.

8. The vessel of claim 7 wherein said headplate has a port for accessing said hollow flexible shaft of said impeller.

9. An impeller comprising a hollow flexible shaft containing a magnet and having a top region and a bottom region, said bottom region having a flexible blade, said magnet is removable through the top of said hollow flexible shaft.

10. The impeller of claim 9 wherein said bottom region comprises two flexible blades.

11. The impeller of claim 9 wherein said impeller is comprised of polyethylene.

12. A method of mixing a fluid comprising the steps of:
    providing a vessel comprising a collapsible bag containing an impeller comprised of a hollow flexible shaft;
    inserting a magnet into said hollow shaft of said impeller;
    introducing an external magnetic source to interact with said magnet and cause said magnet and said hollow shaft to move; and
    removing said magnet through the top of said hollow shaft of said impeller.

13. The method of claim 12 further comprising disposing of said vessel.

14. The method of claim 12 wherein said vessel further comprises a headplate and said hollow flexible shaft of said impeller further comprises a top region and a bottom region, wherein said top region is connected to said headplate.

15. The method of culturing cells in a pre-sterilized vessel comprising a collapsible bag with a headplate and an impeller comprised of a hollow flexible shaft having a top region and a bottom region, wherein said top region is connected to said headplate and wherein said bottom region comprises a flexible blade comprising the steps of the method of:
    inserting a magnet into said hollow shaft of said impeller;
    introducing a cell line and media into said vessel;
    allowing said cell line to proliferate;
    removing said cell line and media from said vessel;
    removing said magnet through the top of said hollow shaft of said impeller; and
    disposing of said vessel.

16. A method of culturing cells in a collapsible vessel containing an impeller having a hollow shaft, the method comprising the steps of:

inserting a magnet into said hollow shaft;

introducing an external magnetic source to interact with said magnet and cause said magnet and said hollow shaft to move; and removing said magnet through the top of said hollow shaft.

17. The method of claim 16 further comprising the step of disposing of said vessel.

18. A vessel comprising:

a headplate having a circumferential edge;

a collapsible bag with an inner surface, an outer surface, and a top periphery, with said top periphery of said bag sealed to said edge of said headplate; and an impeller comprised of a flexible blade and a hollow flexible shaft, said shaft having a top region, a bottom region, and a central axis, said impeller attached to said headplate at said shaft's top region such that said impeller does not rotate about its central axis.

19. The vessel of claim 18 wherein said flexible blade is connected to said bottom region of said shaft.

20. The vessel of claim 19 wherein said flexible blade is contiguous with said shaft.

21. The vessel of claim 18 wherein said shaft contains a magnet.

22. The vessel of claim 18 wherein said top region of said shaft comprises means for restricting movement of said shaft to a periodic pendulum-like rotation.

23. The vessel of claim 22 wherein said means comprises an o-ring.

24. A vessel comprising:

a headplate;

a pre-sterilized collapsible bag sealed to said headplate;

an impeller comprising a hollow flexible shaft connected to said headplate;

two flexible blades attached to said impeller;

an o-ring disposed on said flexible shaft; and a port disposed within said headplate for accessing said hollow flexible shaft of said impeller.

25. A method of mixing the contents of a vessel containing an impeller having a hollow shaft, the method comprising the steps of:

inserting a magnet into the hollow shaft through the top of the hollow shaft; and introducing an external magnetic source to interact with the magnet and cause the magnet and the hollow shaft to move.

26. The method of claim 25 further comprising the step of disposing of said vessel.

27. A method of mixing the contents of a pre-sterilized vessel comprising a collapsible bag with a headplate and an impeller comprised of a hollow flexible shaft having an interior, a top region, and a bottom region, wherein said top region is connected to said headplate such that the interior of said shaft communicates with a hole through said headplate and wherein said bottom region comprises a flexible blade comprising the steps of:

inserting a magnet into the hollow shaft of the impeller through the hole in the headplate;

introducing contents into said vessel;

introducing an external magnetic source to interact with the magnet and cause the magnet and the hollow shaft to move;

allowing said contents to mix;

removing said contents from said vessel; and disposing of said vessel.

* * * * *